United States Patent
Weast et al.

(10) Patent No.: US 9,618,359 B2
(45) Date of Patent: Apr. 11, 2017

(54) WEARABLE SENSOR DATA TO IMPROVE MAP AND NAVIGATION DATA

(71) Applicant: Intel Corporation, Santa Clara, CA (US)

(72) Inventors: John C. Weast, Portland, OR (US); Lenitra M. Durham, Beaverton, OR (US); Giuseppe Raffa, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/497,021

(22) Filed: Sep. 25, 2014

(65) Prior Publication Data
US 2016/0091337 A1    Mar. 31, 2016

(51) Int. Cl.
| | |
|---|---|
| *G01C 22/00* | (2006.01) |
| *G05D 1/00* | (2006.01) |
| *G01C 21/36* | (2006.01) |
| *A61B 5/024* | (2006.01) |
| *G01C 21/34* | (2006.01) |

(52) U.S. Cl.
CPC ...... *G01C 21/3697* (2013.01); *A61B 5/02438* (2013.01); *G01C 21/3453* (2013.01); *G01C 21/3461* (2013.01)

(58) Field of Classification Search
CPC combination set(s) only.
See application file for complete search history.

(56) References Cited

U.S. PATENT DOCUMENTS

| | | | |
|---|---|---|---|
| 5,270,708 A | 12/1993 | Kamishima | |
| 6,459,365 B2 * | 10/2002 | Tamura | G01C 21/3697 340/425.5 |
| 6,529,827 B1 * | 3/2003 | Beason | G01C 5/06 701/4 |
| 2001/0020902 A1 * | 9/2001 | Tamura | G01C 21/3697 340/905 |
| 2004/0196176 A1 * | 10/2004 | Burgett | G01C 5/06 342/120 |
| 2006/0248554 A1 * | 11/2006 | Priddy | G06K 9/00885 725/25 |
| 2007/0106766 A1 | 5/2007 | Collings, III | |

(Continued)

OTHER PUBLICATIONS

"International Application No. PCT/US2015/050446, International Search Report mailed Dec. 18, 2015", 3 pgs.

(Continued)

*Primary Examiner* — Bhavesh V Amin
(74) *Attorney, Agent, or Firm* — Schwegman Lundberg & Woessner, P.A.

(57) ABSTRACT

Various systems and methods for improving map and navigation data are described herein. An electronic navigation system for improving map and navigation data comprises a database access module to access a database of physiological information to obtain a biometric value, the biometric value associated with a location and a time; a processing module to determine whether the biometric value violates a threshold; and a display module to display a notification on a map when the threshold is violated, the map including an area around the location associated with the biometric value, and the notification displayed proximate to the location associated with the biometric value.

23 Claims, 6 Drawing Sheets

(56) References Cited

U.S. PATENT DOCUMENTS

| | | | |
|---|---|---|---|
| 2008/0195978 A1 | 8/2008 | Wissenbach et al. | |
| 2012/0150429 A1* | 6/2012 | Siotos | G01C 21/3617 701/411 |
| 2014/0169751 A1* | 6/2014 | Weast | H04N 5/76 386/200 |

OTHER PUBLICATIONS

"International Application Serial No. PCT/US2015/050446, Written Opinion mailed Dec. 18, 2015", 10 pgs.

* cited by examiner

WEARABLE SENSOR DATA TO IMPROVE MAP AND NAVIGATION DATA

TECHNICAL FIELD

Embodiments described herein generally relate to user interfaces and in particular, to improving map and navigation applications.

BACKGROUND

Positioning systems, such as the Global Positioning System (GPS), provide signals to receivers, which allow the receivers to calculate a position on Earth using trilateration. GPS was originally developed for the U.S. Department of Defense for military and strategic uses. A mechanism called Selective Availability was used to introduce errors so that civilian navigation signals were significantly less accurate than military. In 2000, the Selective Availability mechanism was disabled and GPS signals available to the civilian population became as accurate as those available to military. This highly accurate positioning system, coupled with an influx of mobile devices, allowed for many location-based services to evolve.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

One popular use of positioning systems, such as GPS and GLONASS (Global Navigation Satellite System), is for navigation. With electronic maps, processes to determine potential routes from an origin to a destination, and precise locations, mapping and navigation systems became readily affordable and available for the masses. In more current mobile devices, such as smart phones, maps and navigation applications are bundled with the system software. In addition, many vehicles have navigation systems onboard. While some navigation systems provide route planning based on various aspects such as traffic congestion, weather, or road conditions, what is needed are navigation systems that provide more insight into traffic behavior to inform the driver or provide more intelligent route planning.

In addition, the miniaturization of electronic components is providing the ability to integrate computers, displays, and other informational devices into easy-to-access devices, such as watches, glasses, and other wearable technology. This wearable technology may be used to capture various biometric data, including but not limited to heart rate, skin temperature, brain wave activity, or physical activity (e.g., steps taken, amount of sleep, etc.). Wearable technology may also be used to capture various contextual data, such as environmental data (e.g., air quality, noise levels, etc.). Emotional state, stress level, and other information may be inferred or derived from the data collected. By leveraging health and contextual data captured by wearable devices, and inferential information derived from such data, new insights into route selection and navigation may be accomplished.

Figure 1:
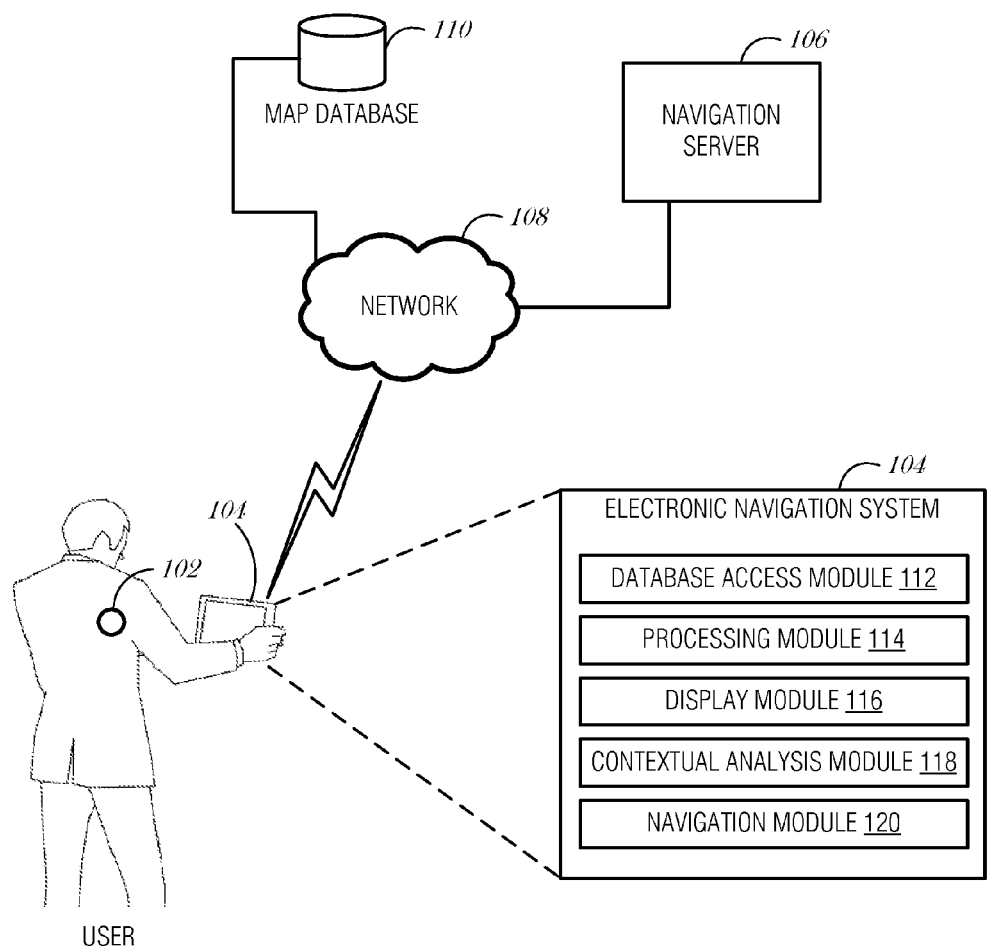
FIG. 1 is a schematic drawing illustrating a networked system, according to an embodiment.

FIG. 1 is a schematic drawing illustrating a networked system 100, according to an embodiment. The networked system 100 includes a physiological sensor 102, an electronic navigation system 104, and a navigation server 106, connected via a network 108. The physiological sensor 102 may be any type of sensor, such as a contact-based sensor, optical sensor, temperature sensor, or the like. The physiological sensor 102 may be adapted to detect a person's heart rate, skin temperature, brain wave activities, alertness (e.g., camera-based eye tracking), activity levels, or other physiological or biological data. The physiological sensor 102 may be integrated into a wearable device, such as a wrist band, glasses, headband, chest strap, shirt, or the like. Alternatively, the physiological sensor 102 may be integrated into a non-wearable system, such as a vehicle (e.g., seat sensor, inward facing cameras, infrared thermometers, etc.) or a bicycle. Several different physiological sensors 102 may be installed or integrated into a wearable or non-wearable device to collect physiological or biological information.

The physiological data collected by the physiological sensor 102 is transmitted to the navigation server 106. The navigation server 106 may include several distinct servers and may include a separate database server. While the navigation server 106 is illustrated as a single device, it is understood that the navigation server 106 may be a cloud server system, a distributed server system, or the like. The navigation server 106 may store or have access to various static maps. The maps may be road maps, satellite imagery, street-view maps, aerial views, or the like. The maps may be served from the navigation server 106 or from a separate server (e.g., a map database 110).

The electronic navigation system 104 may be a standalone device (e.g., a handheld or dash-mounted GPS receiver), a consumer device (e.g., a smartphone, a mobile phone, laptop, etc.), or integrated into a larger system (e.g., an infotainment system in a vehicle). The electronic navigation system 104 may store maps locally or may obtain maps over the network 108, such as from the navigation server 106 or map database 110. The electronic navigation system 104 may calculate routes locally or act as a dumb device and receive routes that are calculated remotely (e.g., at the navigation server 106).

The network 108 includes any type of wired or wireless communication network or combinations of wired or wireless networks. Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or WiMAX networks). The network 108 acts to backhaul the data to the core network (e.g., to the datacenter 106 or other destinations).

During operation, as people drive, walk, run, bike, or otherwise travel, physiological data, contextual data, and other data may be collected. The contextual data may include data such as vehicle telematics data (e.g., braking patterns or force, acceleration, steering history, etc.), weather, date, time, etc. The data may be stored, processed, or otherwise manipulated by the navigation server 106 or another system. When a person in possession of an electronic navigation system 104 traverses a particular area, such as on a road or a trail, the person may be provided a map with an overlay on the electronic navigation system 104. The overlay may include various information, such as the average heart rate of previous hikers, or the aggregate braking patterns of previous drivers. Such information may be useful to the person presently travelling, such as to inform the person of the difficulty of the upcoming portion of the trail or to warn the person of potential road hazards.

In an embodiment, the electronic navigation system 104 is designed for improving map and navigation data and comprises a database access module 112, a processing module 114, and a display module 116. The database access module 112 is to access a database of physiological information to obtain a biometric value, the biometric value associated with a location and a time. In an embodiment, the database of physiological information comprises data obtained from a wearable sensor. The wearable sensor may be integrated into another wearable device (e.g., a watch or glasses) or may be a dedicated wearable sensor (e.g., heart rate monitor chest strap).

The processing module 114 is to determine whether the biometric value violates a threshold. In an embodiment, the threshold comprises a threshold heart rate, and the biometric value comprises heart rates of a plurality of people. In such an embodiment, to determine whether the biometric value violates the threshold, the processing module 114 is to average the heart rates of the plurality of people to obtain an average heart rate for the location and time associated with the biometric value, and compare the average heart rate with the threshold heart rate. Although an average value is discussed, it is understood that other types of mathematical functions may be used, such as a maximum, minimum, variance, integral, etc.

In an embodiment, to determine whether the biometric value violates the threshold, the processing module 114 is to identify a biometric value associated with the current time and determine whether the biometric value associated with the current time violates the threshold. The threshold may be user configurable in some embodiments.

The display module 116 is to display a notification on a map when the threshold is violated, the map including an area around the location associated with the biometric value, and the notification displayed proximate to the location associated with the biometric value. In an embodiment, to display the notification on the map, the display module 116 is to display an icon on the map proximate to the location associated with the biometric value. In an embodiment, the display module 116 is to display a textual overlay on the map proximate to the location associated with the biometric value.

In an embodiment, the display module 116 is to display a portion of the map with a contrasting color proximate to the location associated with the biometric value. In an embodiment, the portion of the map includes a portion of a road displayed on the map. In another embodiment, the portion of the map includes a portion of a hiking trail displayed on the map.

In a further embodiment, the electronic navigation system 104 includes a contextual analysis module 118 to access contextual information associated with the biometric value, the contextual information captured at approximately the location associated with the biometric value. In such an embodiment, the display module 116 is to display a contextual notification on the map, the contextual notification based on the contextual information and positioned proximate to the location associated with the biometric value. In an embodiment, the contextual information comprises vehicle telematics data. Vehicle telematics data may include various vehicle-related data such as braking, steering, gas mileage, or the like. As an example, a portion of a road that is associated with high average heart rates and is also associated with a sharp braking pattern, may indicate a road hazard (e.g., a pothole). This information may be presented by the display module 116.

In an embodiment, the contextual information comprises weather conditions. Weather conditions such as heavy rain, snow, white out conditions, fog, or the like may be identified and presented to the user.

In an embodiment, the contextual information comprises a number of photos taken. For example, a hiking trail may have a certain point where a larger number of photos were taken. This may indicate a scenic overlook, presence of wildlife, or some other point of interest. This metric may be presented in an informational dialog on the displayed route.

In an embodiment, the contextual information comprises an air quality rating. The air quality rating may be obtained from a sensor (e.g., a pollution sensor) or from an external source (e.g., an internet-based environmental conditions monitor, such as airnow.gov). Air quality may be useful for a hiker, biker, walker, or other people who will traverse a route while exposed to the outdoor air unfiltered. Other people with allergies or other respiratory sensitivities may be interested in such a feature.

In an embodiment, the contextual information comprises a noise level. The noise level may be detected by a microphone build into a wearable device. Some people may wish to avoid noisy sections of a road or trail.

In a further embodiment, the electronic navigation system 104 includes a navigation module 120 to obtain a route. In such an embodiment, the display module 116 is to display the route on the map.

In an embodiment, the navigation module 120 is to obtain a different route based on whether the biometric value violates the threshold. For example, a threshold may represent a maximum average heart rate. If a particular portion of a route is associated with a high average heart rate, one that is over the threshold, the navigation module 120 may obtain a different route, one that is less strenuous. In such an embodiment, the display module 116 is to display the different route on the map.

Figure 2:
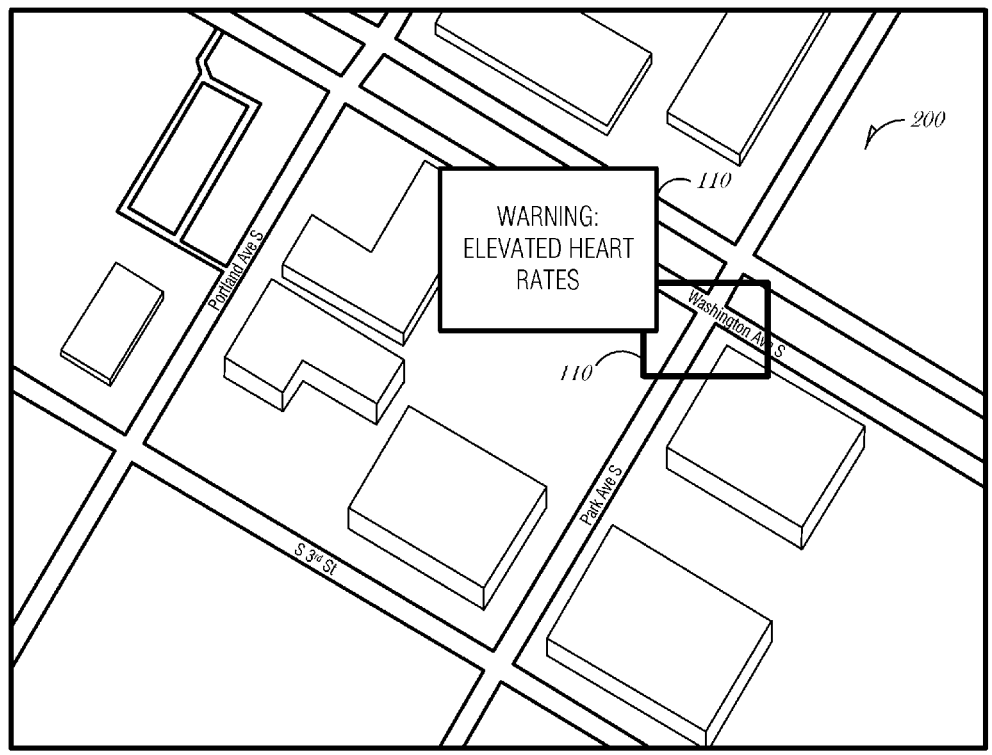
FIG. 2 is an illustration of an example user interface, according to an embodiment.

FIG. 2 is an illustration of an example user interface, according to an embodiment. In FIG. 2, a static map 200 is presented to the user with an overlay, where the overlay includes a text box 202 and an indicator 204. The text box 202 may include various textual and graphical information, such as a warning. The text box 202 may be presented in various forms, such as with a translucent or opaque overlay, a timed presentation (e.g., disappears sometime after appearing), scrolling or animated text or graphics, with various background colors or images, or varying borders or other features. While the text box 202 in FIG. 2 is illustrated as a rectangle, it is understood that any size or shape may be used (e.g., circle, square, rounded corners, three-dimensional, etc.).

The indicator 204 is used to indicate where on the map the particular text box 202 message refers to. In the example shown in FIG. 2, the indicator 204 is a rectangle, although much like the text box 202, the indicator 204 may be of any shape, size, color, or have other features (e.g., animation). The indicator 204 may be color coded such that a red indicator 204 may indicate a high severity of the warning or information, whereas a green indicator 204 may indicate a low severity or some beneficial aspect of the area on the map 200.

With this in mind, FIG. 2 generally indicates that the intersection at Washington and Park is associated with elevated heart rates. The elevated heart rates may be based on a threshold, which may be user defined. Further, the elevated heart rates may be based on recent measurements (e.g., approximately real time data) so that the user is able to see potential hazards. For example, the elevated heart rates may be caused by drivers, pedestrians, or others in the area of Washington and Park who just witnessed a car fire. Alternatively, the elevated heart rates may be based on a historical measurement associated with the present date or time. For example, the user is may view the static map 200 on a particular day or time and see whether elevated heart rates existed based on an occurrence that happened a week, or a month, or a year before.

Figure 3:
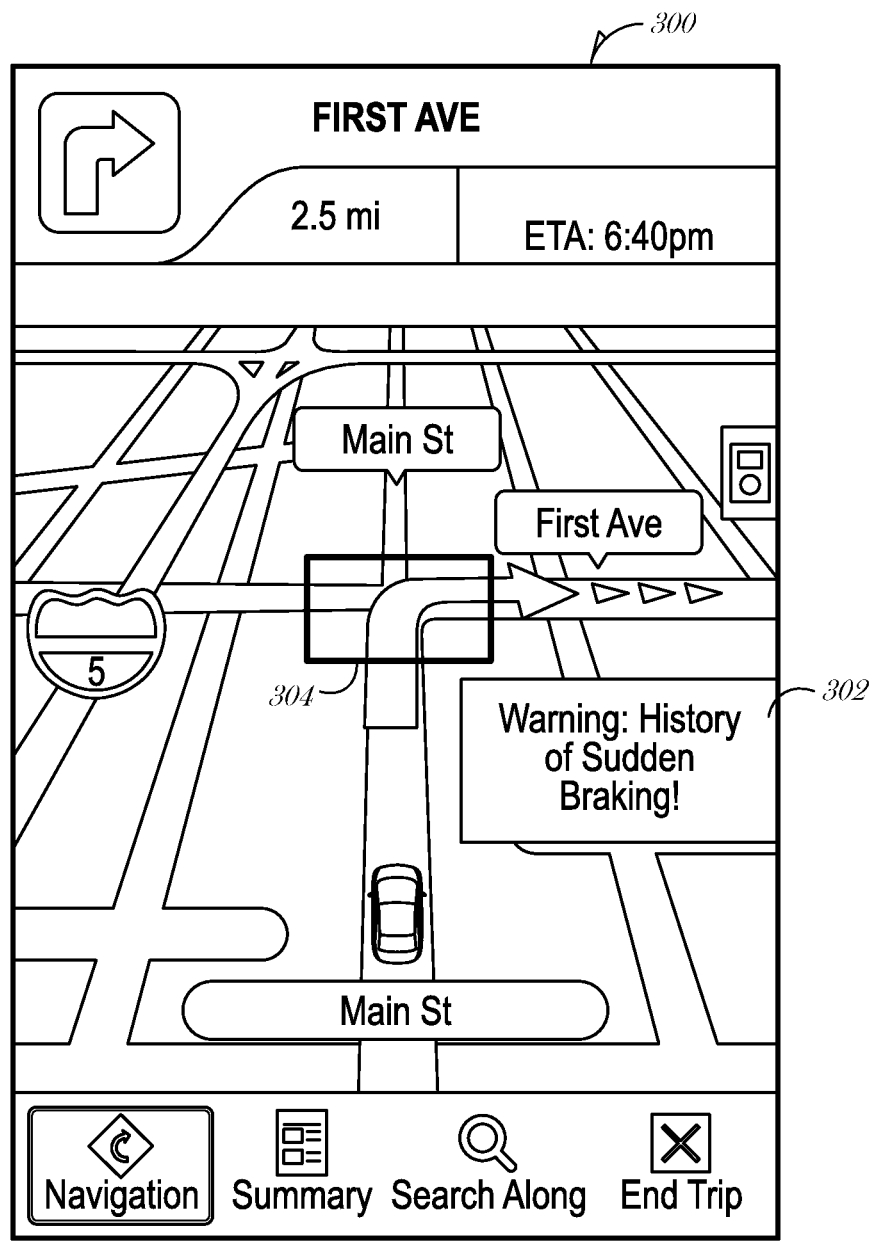
FIG. 3 is an illustration of an example user interface, according to an embodiment.

FIG. 3 is an illustration of an example user interface, according to an embodiment. In FIG. 3, the user is presented a navigation user interface 300 with a route. The user may be presented a text box 302 and indicator 304, similar to those illustrated in FIG. 2. The difference between FIG. 2 and FIG. 3 is that the user interface in FIG. 3 may automatically move, resize, or otherwise manipulate the map as the user traverses the route.

Figure 4:
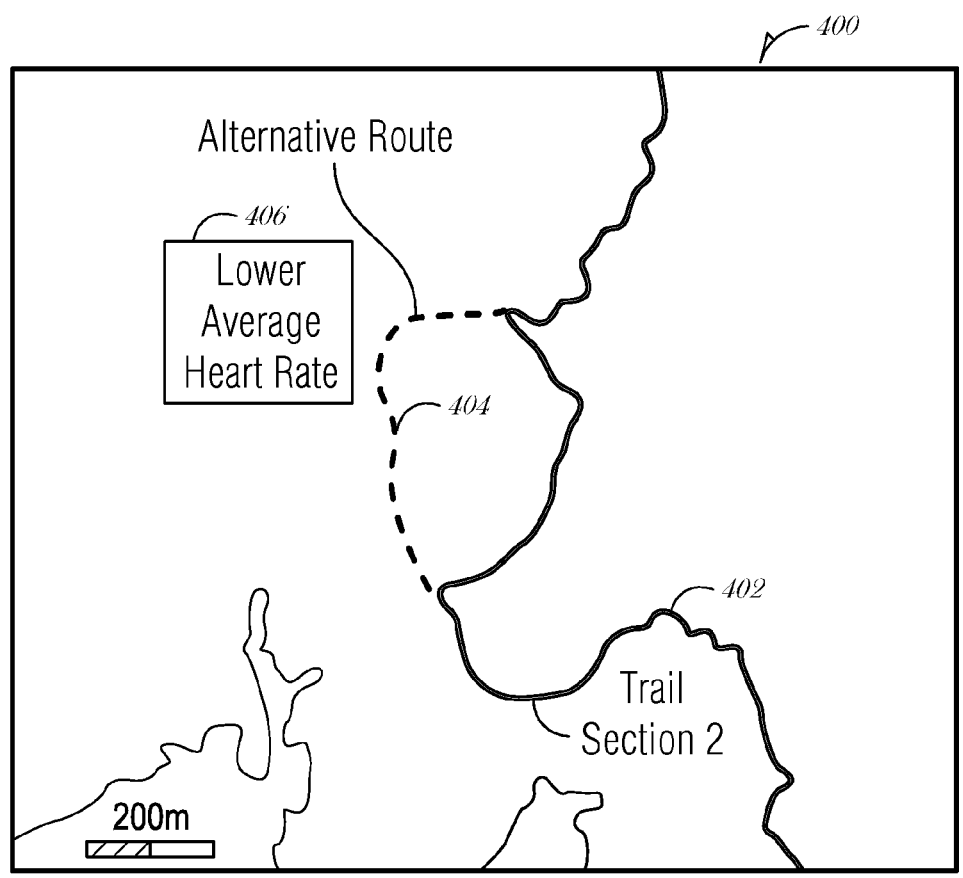
FIG. 4 is another illustration of an example user interface, according to an embodiment.

FIG. 4 is another illustration of an example user interface 400, according to an embodiment. In the user interface 400, a hiking map is shown with a primary trail 402 and an alternative trail 404. The user may be presented the alternative trail with a text box 406 showing the information. This presentation may be in response to a biometric value violating a threshold. The alternative route 404 may be better suited for similar aged or paced hikers, or may route hikers around a sudden change in air quality (as captured from other hikers ahead). Other factors may be used to determine and identify alternative routes, such as by using the number of pictures taken at various points in the route. Such data may indicate likely scenic locations worth a look.

As discussed above, the system leverages the temporality of the context meaning that recommendations may be based on the time of day, month, or year when comparing history or data for the most similar conditions (recurrent event, weather, number of people, demographics of people, physical characteristics of people, etc.) in the past. For example, past data on a marathon would not be a predictor for a pleasant walk in the park—unless of course it is the annual marathon date again.

Figure 5:
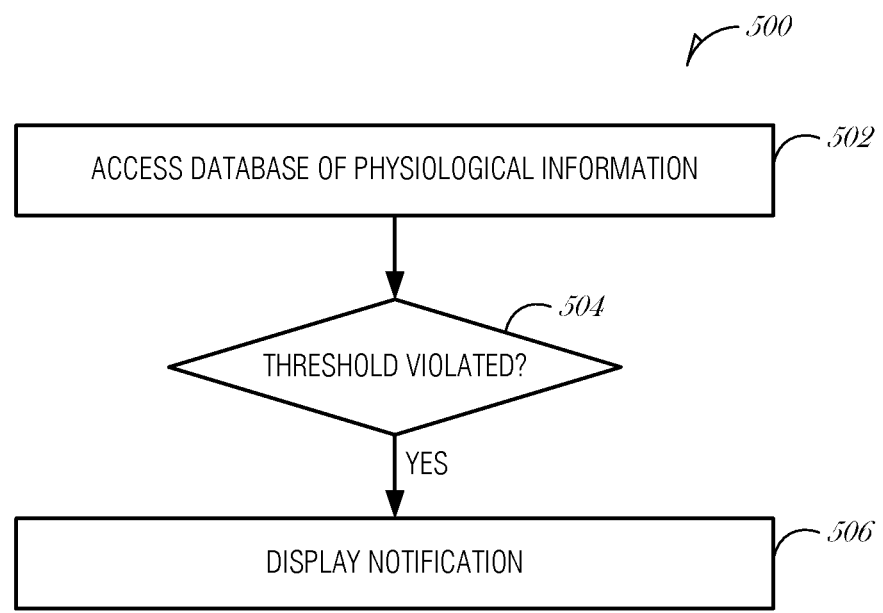
FIG. 5 is a flowchart illustrating a method for improving map and navigation data, according to an embodiment.

FIG. 5 is a flowchart illustrating a method 500 for improving map and navigation data, according to an embodiment. At block 502, a database of physiological information is accessed to obtain a biometric value, the biometric value associated with a location and a time. The database may be accessed by an electronic navigation system. In an embodiment, the database of physiological information comprises data obtained from a wearable sensor.

At block 504, whether the biometric value violates a threshold is determined. In an embodiment, the threshold comprises a threshold heart rate, and the biometric value comprises heart rates of a plurality of people. In such an embodiment, determining whether the biometric value violates the threshold comprises: averaging the heart rates of the plurality of people to obtain an average heart rate for the location and time associated with the biometric value; and comparing the average heart rate with the threshold heart rate.

In an embodiment, determining whether the biometric value violates the threshold comprises: identifying a biometric value associated with the current time and determine whether the biometric value associated with the current time violates the threshold. The threshold may be user configurable in various embodiments.

At block 506, displaying, by the electronic navigation system, a notification on a map when the threshold is violated, the map including an area around the location associated with the biometric value, and the notification displayed proximate to the location associated with the biometric value.

In an embodiment, displaying the notification on the map comprises displaying an icon on the map proximate to the location associated with the biometric value.

In an embodiment, displaying the notification on the map comprises displaying a textual overlay on the map proximate to the location associated with the biometric value.

In an embodiment, displaying the notification on the map comprises displaying a portion of the map with a contrasting color proximate to the location associated with the biometric value. In an embodiment, the portion of the map includes a portion of a road displayed on the map. In an embodiment, the portion of the map includes a portion of a hiking trail displayed on the map.

In a further embodiment, the method 500 includes accessing contextual information associated with the biometric value, the contextual information captured at approximately the location associated with the biometric value; and displaying a contextual notification on the map, the contextual notification based on the contextual information and positioned proximate to the location associated with the biometric value.

In an embodiment, the contextual information comprises vehicle telematics data. In an embodiment, the contextual information comprises weather conditions. In an embodiment, the contextual information comprises a number of photos taken. In an embodiment, the contextual information comprises an air quality rating. In an embodiment, the contextual information comprises a noise level.

In a further embodiment, the method 500 includes obtaining a route and displaying the route on the map. In an embodiment, the method 500 includes obtaining a different route based on whether the biometric value violates the threshold and displaying the different route on the map.

Embodiments may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

Examples, as described herein, may include, or may operate on, logic or a number of components, modules, or mechanisms. Modules may be hardware, software, or firmware communicatively coupled to one or more processors in order to carry out the operations described herein. Modules may be hardware modules, and as such modules may be considered tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software; the general-purpose hardware processor may be configured as respective different modules at different times. Software may accordingly configure a hardware processor, for example, to constitute a particular module at one instance of time and to constitute a different module at a different instance of time. Modules may also be software or firmware modules, which operate to perform the methodologies described herein.

Figure 6:
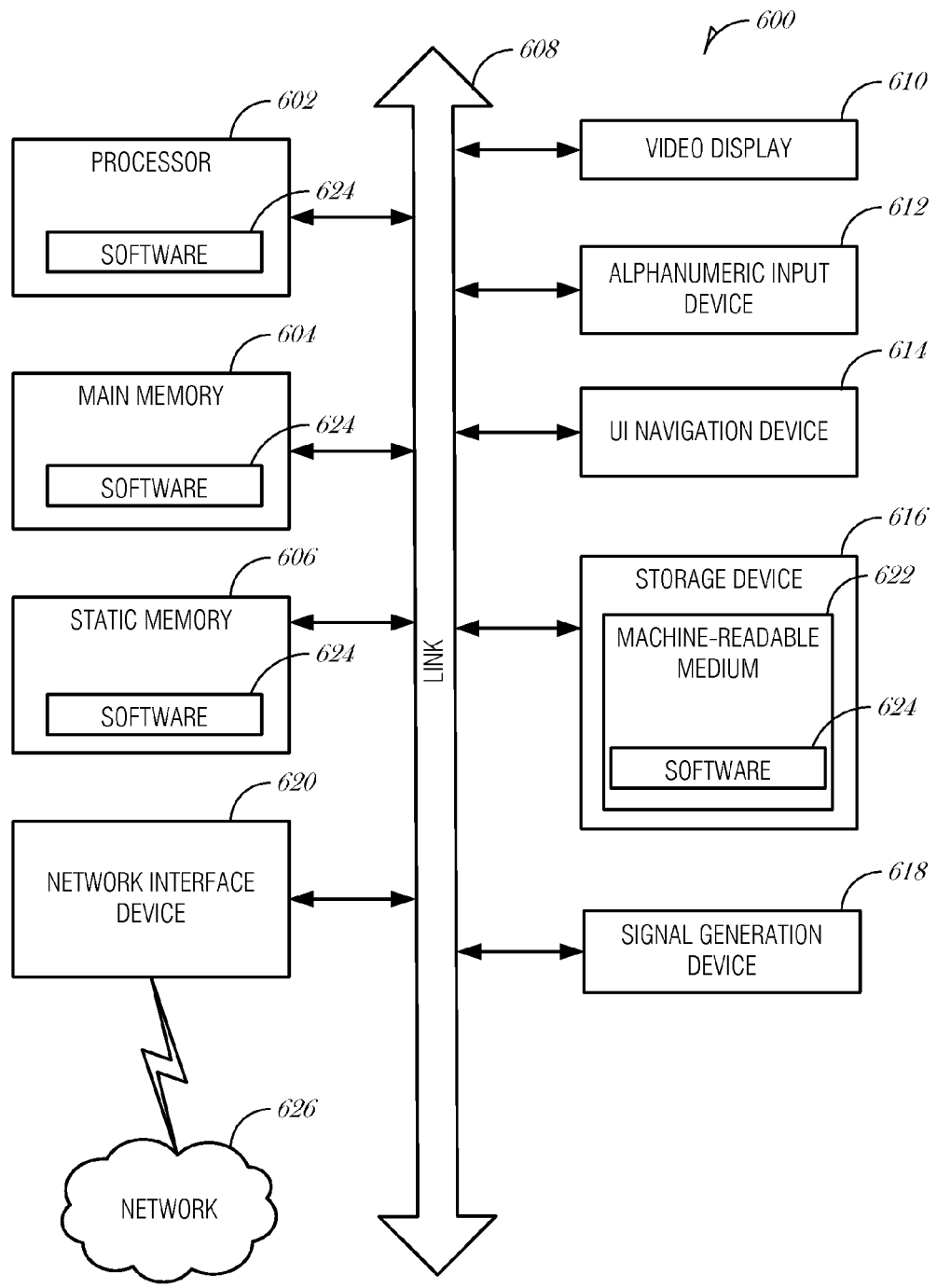
FIG. 6 is a block diagram illustrating an example machine upon which any one or more of the techniques (e.g., methodologies) discussed herein may perform, according to an example embodiment.

FIG. 6 is a block diagram illustrating a machine in the example form of a computer system 600, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be an onboard vehicle system, wearable device, personal computer (PC), a tablet PC, a hybrid tablet, a personal digital assistant (PDA), a mobile telephone, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 600 includes at least one processor 602 (e.g., a central processing unit (CPU), a graphics processing unit (GPU) or both, processor cores, compute nodes, etc.), a main memory 604 and a static memory 606, which communicate with each other via a link 608 (e.g., bus). The computer system 600 may further include a video display unit 610, an alphanumeric input device 612 (e.g., a keyboard), and a user interface (UI) navigation device 614 (e.g., a mouse). In one embodiment, the video display unit 610, input device 612 and UI navigation device 614 are incorporated into a touch screen display. The computer system 600 may additionally include a storage device 616 (e.g., a drive unit), a signal generation device 618 (e.g., a speaker), a network interface device 620, and one or more sensors (not shown), such as a global positioning system (GPS) sensor, compass, accelerometer, or other sensor.

The storage device 616 includes a machine-readable medium 622 on which is stored one or more sets of data structures and instructions 624 (e.g., software) embodying or utilized by any one or more of the methodologies or functions described herein. The instructions 624 may also reside, completely or at least partially, within the main memory 604, static memory 606, and/or within the processor 602 during execution thereof by the computer system 600, with the main memory 604, static memory 606, and the processor 602 also constituting machine-readable media.

While the machine-readable medium 622 is illustrated in an example embodiment to be a single medium, the term "machine-readable medium" may include a single medium or multiple media (e.g., a centralized or distributed database, and/or associated caches and servers) that store the one or more instructions 624. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Additional Notes & Examples

Example 1 includes subject matter for improving map and navigation data (such as a device, apparatus, or machine) comprising: a database access module to access a database of physiological information to obtain a biometric value, the biometric value associated with a location and a time; a processing module to determine whether the biometric value violates a threshold; and a display module to display a notification on a map when the threshold is violated, the map including an area around the location associated with the biometric value, and the notification displayed proximate to the location associated with the biometric value.

In Example 2, the subject matter of Example 1 may include, wherein the threshold comprises a threshold heart rate, and wherein the biometric value comprises heart rates of a plurality of people, and wherein to determine whether the biometric value violates the threshold, the processing module is to: average the heart rates of the plurality of people to obtain an average heart rate for the location and time associated with the biometric value; and compare the average heart rate with the threshold heart rate.

In Example 3, the subject matter of any one or more of Examples 1 to 2 may include, wherein to determine whether the biometric value violates the threshold, the processing module is to: identify a biometric value associated with the current time; and determine whether the biometric value associated with the current time violates the threshold.

In Example 4, the subject matter of any one or more of Examples 1 to 3 may include, wherein the threshold is user configurable.

In Example 5, the subject matter of any one or more of Examples 1 to 4 may include, a contextual analysis module to: access contextual information associated with the biometric value, the contextual information captured at approximately the location associated with the biometric value; and wherein the display module is to display a contextual notification on the map, the contextual notification based on the contextual information and positioned proximate to the location associated with the biometric value.

In Example 6, the subject matter of any one or more of Examples 1 to 5 may include, wherein the contextual information comprises vehicle telematics data.

In Example 7, the subject matter of any one or more of Examples 1 to 6 may include, wherein the contextual information comprises weather conditions.

In Example 8, the subject matter of any one or more of Examples 1 to 7 may include, wherein the contextual information comprises a number of photos taken.

In Example 9, the subject matter of any one or more of Examples 1 to 8 may include, wherein the contextual information comprises an air quality rating.

In Example 10, the subject matter of any one or more of Examples 1 to 9 may include, wherein the contextual information comprises a noise level.

In Example 11, the subject matter of any one or more of Examples 1 to 10 may include, wherein to display the notification on the map, the display module is to display an icon on the map proximate to the location associated with the biometric value.

In Example 12, the subject matter of any one or more of Examples 1 to 11 may include, wherein to display the notification on the map, the display module is to display a textual overlay on the map proximate to the location associated with the biometric value.

In Example 13, the subject matter of any one or more of Examples 1 to 12 may include, wherein to display the notification on the map, the display module is to display a portion of the map with a contrasting color proximate to the location associated with the biometric value.

In Example 14, the subject matter of any one or more of Examples 1 to 13 may include, wherein the portion of the map includes a portion of a road displayed on the map.

In Example 15, the subject matter of any one or more of Examples 1 to 14 may include, wherein the portion of the map includes a portion of a hiking trail displayed on the map.

In Example 16, the subject matter of any one or more of Examples 1 to 15 may include, a navigation module to obtain a route, wherein the display module is to display the route on the map.

In Example 17, the subject matter of any one or more of Examples 1 to 16 may include, wherein the navigation module is to obtain a different route based on whether the biometric value violates the threshold, and wherein the display module is to display the different route on the map.

In Example 18, the subject matter of any one or more of Examples 1 to 17 may include, wherein the database of physiological information comprises data obtained from a wearable sensor.

Example 19 includes subject matter for improving map and navigation data (such as a method, means for performing acts, machine readable medium including instructions that when performed by a machine cause the machine to performs acts, or an apparatus to perform) comprising a method for improving map and navigation data, the method comprising: accessing, by an electronic navigation system, a database of physiological information to obtain a biometric value, the biometric value associated with a location and a time; determining whether the biometric value violates a threshold; and displaying, by the electronic navigation system, a notification on a map when the threshold is violated, the map including an area around the location associated with the biometric value, and the notification displayed proximate to the location associated with the biometric value.

In Example 20, the subject matter of Example 19 may include, wherein the threshold comprises a threshold heart rate, and wherein the biometric value comprises heart rates of a plurality of people, and wherein determining whether the biometric value violates the threshold comprises: averaging the heart rates of the plurality of people to obtain an average heart rate for the location and time associated with the biometric value; and comparing the average heart rate with the threshold heart rate.

In Example 21, the subject matter of any one or more of Examples 19 to 20 may include, wherein determining whether the biometric value violates the threshold comprises: identifying a biometric value associated with the current time; and determining whether the biometric value associated with the current time violates the threshold.

In Example 22, the subject matter of any one or more of Examples 19 to 21 may include, wherein the threshold is user configurable.

In Example 23, the subject matter of any one or more of Examples 19 to 22 may include, accessing contextual information associated with the biometric value, the contextual information captured at approximately the location associated with the biometric value; and displaying a contextual notification on the map, the contextual notification based on the contextual information and positioned proximate to the location associated with the biometric value.

In Example 24, the subject matter of any one or more of Examples 19 to 23 may include, wherein the contextual information comprises vehicle telematics data.

In Example 25, the subject matter of any one or more of Examples 19 to 24 may include, wherein the contextual information comprises weather conditions.

In Example 26, the subject matter of any one or more of Examples 19 to 25 may include, wherein the contextual information comprises a number of photos taken.

In Example 27, the subject matter of any one or more of Examples 19 to 26 may include, wherein the contextual information comprises an air quality rating.

In Example 28, the subject matter of any one or more of Examples 19 to 27 may include, wherein the contextual information comprises a noise level.

In Example 29, the subject matter of any one or more of Examples 19 to 28 may include, wherein displaying the notification on the map comprises displaying an icon on the map proximate to the location associated with the biometric value.

In Example 30, the subject matter of any one or more of Examples 19 to 29 may include, wherein displaying the notification on the map comprises displaying a textual overlay on the map proximate to the location associated with the biometric value.

In Example 31, the subject matter of any one or more of Examples 19 to 30 may include, wherein displaying the notification on the map comprises displaying a portion of the map with a contrasting color proximate to the location associated with the biometric value.

In Example 32, the subject matter of any one or more of Examples 19 to 31 may include, wherein the portion of the map includes a portion of a road displayed on the map.

In Example 33, the subject matter of any one or more of Examples 19 to 32 may include, wherein the portion of the map includes a portion of a hiking trail displayed on the map.

In Example 34, the subject matter of any one or more of Examples 19 to 33 may include, obtaining a route; and displaying the route on the map.

In Example 35, the subject matter of any one or more of Examples 19 to 34 may include, obtaining a different route based on whether the biometric value violates the threshold; and displaying the different route on the map.

In Example 36, the subject matter of any one or more of Examples 19 to 35 may include, wherein the database of physiological information comprises data obtained from a wearable sensor.

Example 37 includes a machine-readable medium including instructions, which when executed by a machine, cause the machine to perform operations of any of the methods of Examples 19-36.

Example 38 includes an apparatus comprising means for performing any of the methods of Examples 19-36.

Example 39 includes an apparatus for improving map and navigation data, comprising: means for accessing, by an electronic navigation system, a database of physiological information to obtain a biometric value, the biometric value associated with a location and a time; means for determining whether the biometric value violates a threshold; and means for displaying, by the electronic navigation system, a notification on a map when the threshold is violated, the map including an area around the location associated with the biometric value, and the notification displayed proximate to the location associated with the biometric value.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. An electronic navigation system for improving map and navigation data, the system comprising:
   a database access module to access a database of physiological information to obtain a biometric value, the biometric value associated with a location and a time;
   a contextual analysis module to access contextual information associated with the biometric value, the contextual information captured at approximately the location associated with the biometric value;
   a processing module to determine whether the biometric value violates a threshold; and
   a display module to display a notification on a map when the threshold is violated, the map including an area around the location associated with the biometric value, and the notification displayed proximate to the location associated with the biometric value, wherein the display module is to display a contextual notification on the map, the contextual notification based on the contextual information and positioned proximate to the location associated with the biometric value.

2. The electronic navigation system of claim 1, wherein the threshold comprises a threshold heart rate, and wherein the biometric value comprises heart rates of a plurality of people, and wherein to determine whether the biometric value violates the threshold, the processing module is to:
average the heart rates of the plurality of people to obtain an average heart rate for the location and time associated with the biometric value; and
compare the average heart rate with the threshold heart rate.

3. The electronic navigation system of claim 1, wherein to determine whether the biometric value violates the threshold, the processing module is to:
identify a biometric value associated with the current time; and
determine whether the biometric value associated with the current time violates the threshold.

4. The electronic navigation system of claim 1, wherein the threshold is user configurable.

5. The electronic navigation system of claim 1, wherein the contextual information comprises vehicle telematics data.

6. The electronic navigation system of claim 1, wherein the contextual information comprises weather conditions.

7. The electronic navigation system of claim 1, wherein the contextual information comprises a number of photos taken.

8. The electronic navigation system of claim 1, wherein the contextual information comprises an air quality rating.

9. The electronic navigation system of claim 1, wherein the contextual information comprises a noise level.

10. The electronic navigation system of claim 1, wherein to display the notification on the map, the display module is to display an icon on the map proximate to the location associated with the biometric value.

11. The electronic navigation system of claim 1, wherein to display the notification on the map, the display module is to display a textual overlay on the map proximate to the location associated with the biometric value.

12. The electronic navigation system of claim 1, wherein to display the notification on the map, the display module is to display a portion of the map with a contrasting color proximate to the location associated with the biometric value.

13. The electronic navigation system of claim 12, wherein the portion of the map includes a portion of a road displayed on the map.

14. The electronic navigation system of claim 12, wherein the portion of the map includes a portion of a hiking trail displayed on the map.

15. The electronic navigation system of claim 1, further comprising a navigation module to obtain a route, wherein the display module is to display the route on the map.

16. The electronic navigation system of claim 15, wherein the navigation module is to obtain a different route based on whether the biometric value violates the threshold, and wherein the display module is to display the different route on the map.

17. The electronic navigation system of claim 1, wherein the database of physiological information comprises data obtained from a wearable sensor.

18. A method for improving map and navigation data, the method comprising:
accessing, by an electronic navigation system, a database of physiological information to obtain a biometric value, the biometric value associated with a location and a time;
accessing contextual information associated with the biometric value, the contextual information captured at approximately the location associated with the biometric value;
determining whether the biometric value violates a threshold;
displaying, by the electronic navigation system, a notification on a map when the threshold is violated, the map including an area around the location associated with the biometric value, and the notification displayed proximate to the location associated with the biometric value; and
displaying a contextual notification on the map, the contextual notification based on the contextual information and positioned proximate to the location associated with the biometric value.

19. The method of claim 18, wherein the threshold comprises a threshold heart rate, and wherein the biometric value comprises heart rates of a plurality of people, and wherein determining whether the biometric value violates the threshold comprises:
averaging the heart rates of the plurality of people to obtain an average heart rate for the location and time associated with the biometric value; and
comparing the average heart rate with the threshold heart rate.

20. The method of claim 18, wherein determining whether the biometric value violates the threshold comprises:
identifying a biometric value associated with the current time; and
determining whether the biometric value associated with the current time violates the threshold.

21. At least one non-transitory machine-readable medium including instructions for improving map and navigation data, which when executed by a machine, cause the machine to:
access a database of physiological information to obtain a biometric value, the biometric value associated with a location and a time;
access contextual information associated with the biometric value, the contextual information captured at approximately the location associated with the biometric value;
determine whether the biometric value violates a threshold; and
display a notification on a map, the map including an area around the location associated with the biometric value, and the notification displayed proximate to the location associated with the biometric value; and
display a contextual notification on the map, the contextual notification based on the contextual information and positioned proximate to the location associated with the biometric value.

22. The at least one machine-readable medium of claim 21, wherein the threshold comprises a threshold heart rate, and wherein the biometric value comprises heart rates of a plurality of people, and wherein the instructions to determine whether the biometric value violates the threshold comprise instructions to:

average the heart rates of the plurality of people to obtain an average heart rate for the location and time associated with the biometric value; and compare the average heart rate with the threshold heart rate.

23. The at least one machine-readable medium of claim 21, wherein the instructions to determine whether the biometric value violates the threshold comprise instructions to:

identify a biometric value associated with the current time; and determine whether the biometric value associated with the current time violates the threshold.

* * * * *